(12) United States Patent
Gorman et al.

(10) Patent No.: US 6,367,328 B1
(45) Date of Patent: Apr. 9, 2002

(54) NONINVASIVE DETECTION OF CORROSION, MIC, AND FOREIGN OBJECTS IN FLUID-FILLED CONTAINERS USING LEAKY GUIDED ULTRASONIC WAVES

(75) Inventors: Michael R. Gorman, Englewood; Steven M. Ziola, Littleton; Wei Huang, Highlands Ranch, all of CO (US)

(73) Assignee: Digital Wave Corporation, Englewood, CO (US)

( * ) Notice: Subject to any disclaimer, the term of this patent is extended or adjusted under 35 U.S.C. 154(b) by 0 days.

(21) Appl. No.: 09/613,704

(22) Filed: Jul. 11, 2000

Related U.S. Application Data (60) Provisional application No. 60/143,366, filed on Jul. 12, 1999, provisional application No. 60/203,661, filed on May 12, 2000, and provisional application No. 60/209,796, filed on Jun. 7, 2000.

(51) Int. Cl.⁷ .................................................. G01N 29/00
(52) U.S. Cl. .................. 73/592; 73/598; 73/290 R; 73/622; 73/624; 73/597; 73/644
(58) Field of Search .................. 73/570, 597, 599, 73/52, 587, 590, 290 R, 620, 622, 624, 643, 644, 600, 598, 592

(56) References Cited

U.S. PATENT DOCUMENTS

| | | | | |
|---|---|---|---|---|
| 4,843,884 A | * | 7/1989 | House et al. | 73/622 |
| 4,890,496 A | * | 1/1990 | Birring et al. | 73/597 |
| 5,031,456 A | * | 7/1991 | Askwith et al. | 73/587 |
| 5,295,120 A | * | 3/1994 | McShane | 367/188 |
| 5,526,689 A | * | 6/1996 | Coulter et al. | 73/592 |
| 5,723,791 A | * | 3/1998 | Koch et al. | 73/597 |
| 5,734,588 A | * | 3/1998 | Rose et al. | 73/644 |
| 5,767,410 A | * | 6/1998 | Lareau et al. | 73/623 |
| 5,922,945 A | * | 7/1999 | Allmaras et al. | 73/52 |
| 5,970,434 A | * | 10/1999 | Brophy et al. | 73/584 |
| 6,105,431 A | * | 8/2000 | Duffil et al. | 73/624 |
| 6,186,004 B1 | * | 2/2001 | Kaduchak et al. | 73/596 |

* cited by examiner

Primary Examiner—Hezron Williams
Assistant Examiner—Jacques Saint-Surin
(74) Attorney, Agent, or Firm—Jonathan Alan Quine; Quine Intellectual Property Law Group, P.C.

(57) ABSTRACT

Ultrasonic energy in the form of guided waves is launched into the wall of a fluid-filled container. The guided wave propagates around the circumference of the container from a transmitting transducer to a receiving transducer. Part of the guide wave energy leaks into the fluid in the form of bulk waves, reflects off the inner wall on the other side and enters back to the receiving transducer trailing the direct wave. Analysis of the received waves determines the presence of corrosion pitting and MIC nodules on the container inner wall, and fluid level. In addition, it determines whether foreign objects are inside the container. The guided waves are created with wideband transducers excited at certain frequencies that depend on the material and geometry of the part being measured. The leakage energy is maximized with a shaped tone burst pulse at the specified frequency. The energy and energy ratio of both the direct and leakage fields are measured and related to the container inner wall condition and the presence of any foreign objects in the fluid.

40 Claims, 2 Drawing Sheets

NONINVASIVE DETECTION OF CORROSION, MIC, AND FOREIGN OBJECTS IN FLUID-FILLED CONTAINERS USING LEAKY GUIDED ULTRASONIC WAVES

CROSS REFERENCE TO RELATED APPLICATIONS

This application is related to "NONINVASIVE DETECTION OF CORROSION, MIC, AND FOREIGN OBJECTS IN FLUID-FILLED PIPES USING LEAKY GUIDED ULTRASONIC WAVES" by Gorman et al., U.S. Provisional Application No. 60/143,366, filed Jul. 12, 1999 and to "NONINVASIVE DETECTION OF CORROSION, MIC, AND FOREIGN OBJECTS IN FLUID-FILLED PIPES USING LEAKY GUIDED ULTRASONIC WAVES" by Gorman et al., U.S. Provisional Application No. 60/203,661, filed May 12, 2000. This application is also related to "NONINVASIVE DETECTION OF CORROSION, MIC, AND FOREIGN OBJECTS IN PIPES USING GUIDED ULTRASONIC WAVES" by Gorman and Ziola, U.S. Provisional Application No. 60/209,796, filed Jun. 7, 2000 and to "NONINVASIVE DETECTION OF CORROSION, MIC, AND FOREIGN OBJECTS IN PIPES USING GUIDED ULTRASONIC WAVES" by Gorman and Ziola, Ser. No. 08/613,705, filed Jul. 11, 2000. This application claims priority to each of these prior applications, pursuant to 35 U.S.C. §119(e), as well as any other applicable rule or statute.

FIELD OF INVENTION

This invention relates to noninvasive testing of the internal conditions of fluid-filled containers such as pipes, cylinders, etc., and to novel ultrasonic methods for testing these internal conditions.

COPYRIGHT NOTICE

Pursuant to 37 C.F.R. 1.71(e), Applicants note that a portion of this disclosure contains material which is subject to copyright protection. The copyright owner has no objection to the facsimile reproduction by anyone of the patent document or patent disclosure, as it appears in the Patent and Trademark Office patent file or records, but otherwise reserves all copyright rights whatsoever.

BACKGROUND OF THE INVENTION

Detecting inner wall corrosion in containers such as pipes, conduits, cylinders, tanks, pressure vessels, etc. has been a longstanding concern in many industries. For example, MIC (microbiologically influenced corrosion) in water systems is of particular concern. Microbes live in water everywhere and are difficult to kill. Corrosion pitting, slimy fluid and rusty nodules are often the products of MIC. Such corrosion and foreign objects cause wall thinning and reduction of flow area that are detrimental to the structural performance of pipes or other containers, and can sometimes lead to disastrous consequences. Chemical, petroleum, water utility, fire and power industries have been battling MIC and other forms of internal container (e.g., pipe) corrosion (e.g., in water and other fluid storage and/or conducting systems) for many years.

Many nondestructive or noninvasive methods have been applied, with varying degrees of success, to locating MIC and assessing its effects. X-ray and gamma ray radiographs provide images that can be used to gauge the presence of MIC, the amount of occlusion and wall thinning. However, drawbacks of these methods include slow inspection speed, high cost and safety/health concern issues.

Ultrasonic thickness gauging is used routinely to measure wall thickness in refinery piping and tanks. Compared to radiography, ultrasound is cheaper and doesn't emit harmful radiation. A single thickness gauge measurement is much faster than radiography, but it only covers a localized area the size of the transducer used in the measurement. Thus, to obtain the thickness information over a large area, the ultrasonic thickness gauge method may not be as fast as radiographic methods. More importantly, a wall thickness reading at a given point depends on good through-thickness echoes so that an accurate time can be measured. Rough corroded internal wall surface and porous MIC nodules make it difficult to get a valid reading. Often the wall thickness reading is greater than nominal. In some cases, no echoes are available because the ultrasonic energy is simply absorbed or scattered. The ultrasonic thickness gauge is not used to detect the existence of, e.g., slimy fluid either.

The present invention overcomes these and other limitations of the prior art by providing new methods, apparatus and integrated systems for measuring features of fluid filled containers (e.g., pipes, tanks, barrels, drums, cylinders, plates and other structures) and a variety of other features that will become apparent upon complete review of the following.

SUMMARY OF THE INVENTION

A "leaky guided wave ultrasound" (LGWU) method is provided for fast and reliable detection of features on the internal walls of containers (e.g., pipes, conduits, tanks, barrels, drums, cylinders, plates and other appropriate structures that will be apparent upon further review of the following), such as container wall irregularities, loss of wall material, pitting, corrosion, MIC, or the like, as well as for the detection of foreign objects, e.g., in fluid-filled containers. Material in the pipes, whether deliberate (e.g., container structural features) or unintended (e.g., ice or foreign objects) can also be detected.

The methods, devices and systems herein are generally applicable to structures and systems that can be configured to comprise one or more gas, solid or fluid. The methods, systems and devices herein are particularly well-suited to structures and systems comprising fluid filled containers.

In the methods of the invention, a transmitting transducer (e.g., placed circumferentially on the outside of the container) excites a guided wave, and part of its energy leaks into a material such as a fluid in a container. The leaking wave travels through the fluid or other material, reflects off the container inner wall and enters the receiving transducer.

The LGWU method measures both the direct field, and the leakage field inside the fluid generated by the guided ultrasonic waves. Since the leakage field interacts directly and, typically, only, with the fluid and inner container wall, the LGWU method is able to reliably detect corrosion, MIC and other features on container inner walls (e.g., the insides of pipes), as well as fluid level and composition, including foreign objects inside the fluid.

By calibrating against the measured direct field, the LGWU method is not sensitive to the container outside wall surface condition, such as the existence of paint, rust or dust. In addition, a single LGWU measurement covers a significant portion of the circumference of the container. Therefore, as few as two or three LGWU measurement locations can provide approximately 100% inspection coverage of an entire container circumference. Thus, the inspection speed is faster than any prior methods. The LGWU method can also be used to accurately detect fluid level (e.g., whether water, hydrocarbon or other fluid type) in the container, or the existence of ice in the container, e.g., due to frozen condensation water.

The present invention also provides devices, apparatus, integrated systems and kits for practicing the methods of the invention. For example, the invention provides an integrated system and/or device for detecting corrosion and MIC on the inner wall of fluid-filled containers such as pipes, foreign objects in the fluid, and/or fluid level using leaky guided wave ultrasound (LGWU).

The system/device includes components for performing the method above, such as a transmitting transducer and a receiving transducer or a single pulse-echo transducer configured for placement at circumferential or longitudinal positions of a fluid-filled container, a wave generator or pulser which produces a shaped tone burst pulse at a specified frequency or uses a resonant transducer excited by a spike or rectangular pulse to create the specified frequency and detection modules consisting of a receiving transducer or transducers connected to both digital and analog amplifiers and filters, analog to digital converters controlled by software or firmware and digital electronic storage media for the purpose of measuring both a direct field and a leakage field, software and/or firmware for analyzing the direct and leakage field signals, thereby providing an indication of existence of corrosion and MIC on the container inner wall, foreign objects inside the fluid and fluid level.

The guided wave can be excited at a selected frequency and angle to maximize the leakage field for selected container ODs and materials. Other suitable wave characteristics can also be selected or modulated in the methods and systems herein; e.g., the amplitude of a given phase point on the tone bursts can be modulated or selected.

The device, apparatus, kit or system can include a computer or computer readable medium having an instruction set for controlling the system e.g., for controlling the transmitting transducer the guided wave generator, or the like. The computer or computer readable medium (or multiple associated computers or computer media) can include other relevant instruction sets, e.g., for measuring the direct field and the leakage field, reporting the results of the measurement to a user, running a graphical display of the relevant results, or the like. Kits can include any of the apparatus or integrated systems elements plus containers for storing the apparatus or system elements, instructions in using the apparatus or integrated systems elements, e.g., to practice the methods herein, packaging, etc.

A presently preferred method/system is to use an arbitrary function generator (which, e.g., generates a pulse at a user-defined frequency) in combination with a wideband transducer, so that a range of frequencies can be excited and received. This approach typically uses computer software to control and shape the pulse and frequency along with wideband amplifiers and filters. The system device includes the geometrical configurations and various media that can be used to couple the transducers to the container, tank or structure.

Further objects and advantages of the invention will become apparent from a consideration of the drawings and description.

DETAILED DISCUSSION OF THE INVENTION

List of Reference Numerals

The reference numerals below correspond to elements of the figures.

Figure 1:
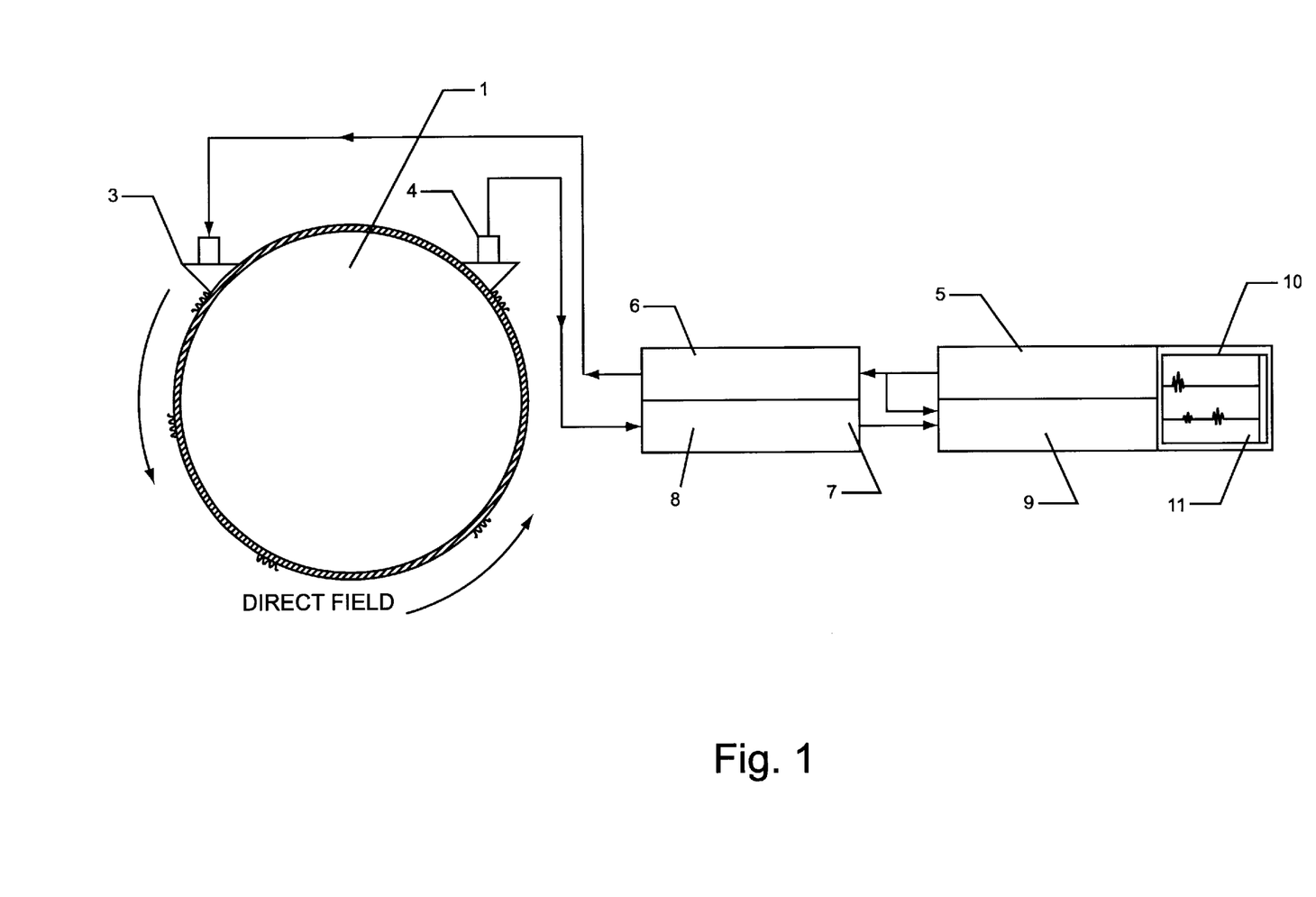
FIG. 1 is a schematic of the LGWU measurement system.
Figure 2:
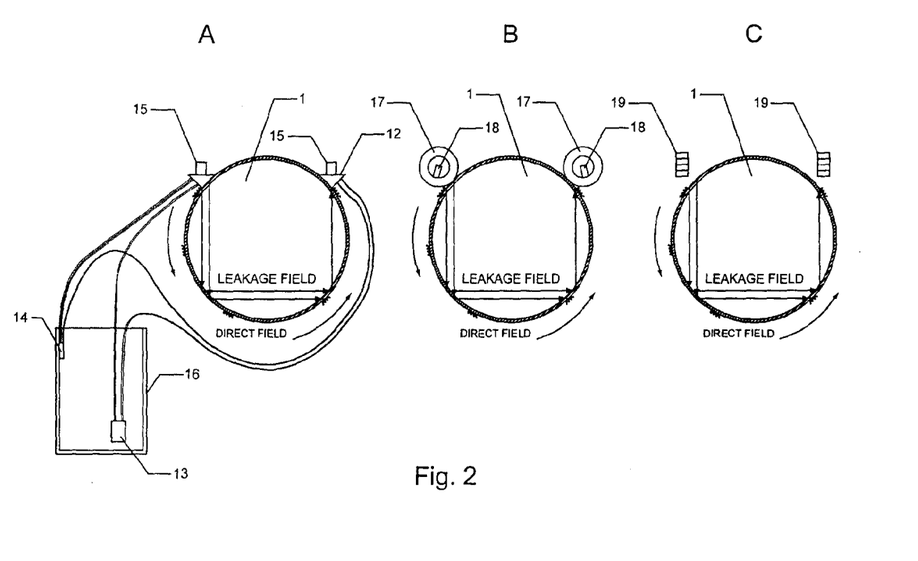
FIG. 2 panels A–C is a schematic of three different ways of implementing the LGWU transducer coupling system 3 and 4 in FIG. 1.
Figure 2A:
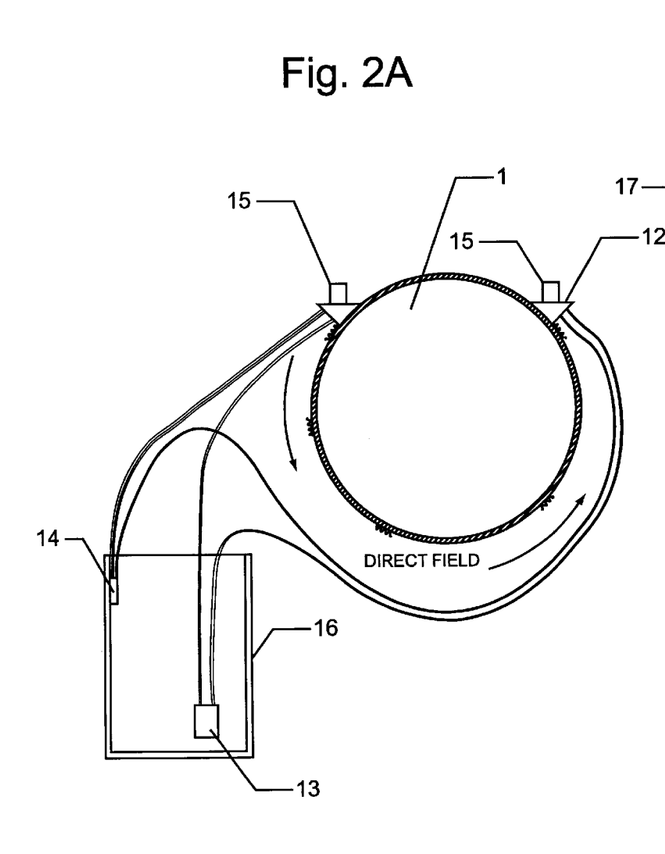
Figures 2B, 2C:
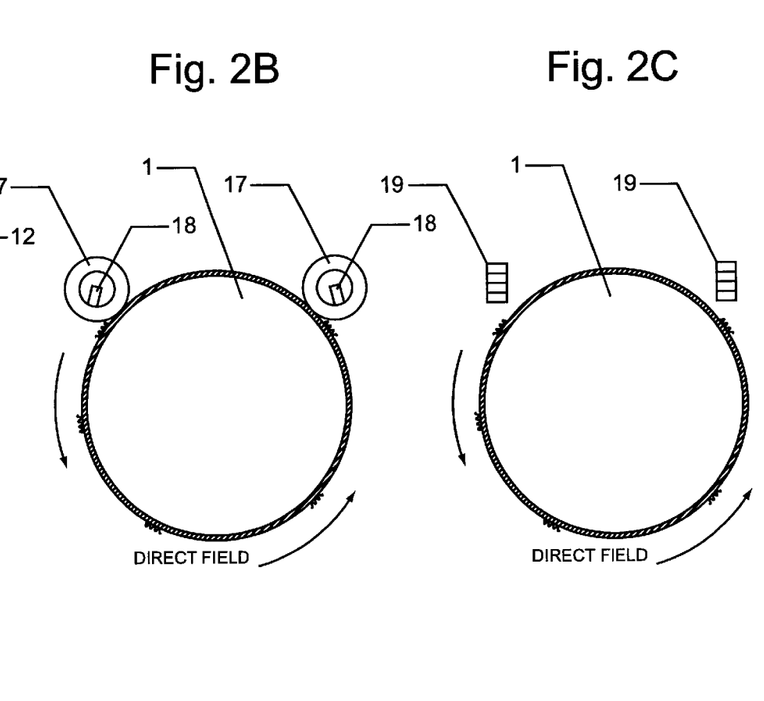

1—fluid filled pipe or other container
3—transmitting transducer coupling system
4—receiving transducer coupling system
5—arbitrary function generator
6—RF amplifier
7—RF receiver—gain circuitry
8—RF receiver—filter circuitry
9—2-channel A/D converter
10—computer
11—energy field detection/display module comprising LGWU elements
12—wedge shoe
13—water pump
14—vacuum pump
15—contact transducer
16—water bucket
17—rubber wheel
18—immersion transducer
19—Air-coupled transducer Introduction: Guided Wave Ultrasonic Testing Guided ultrasonic waves can be used to overcome the speed limitation of a standard ultrasonic thickness gauge. The standard thickness gauge involves a standard "flashlight" beam pulse-echo ultrasonic testing (UT) at a point, with only one transducer being used as both the transmitter and receiver.

In contrast, a guided wave ultrasound (GWU) travels in the areal direction along the axis or circumference of the pipe or other container wall, rather than in the thickness direction. Typically, two transducers placed on the wall surface, several inches apart are used in GWU; one acts as the transmitter and the other as the receiver.

The physics of these different approaches is quite different, as might be expected. Standard UT involves bulk or free waves at wavelengths much smaller than the wall thickness, and the waves can be treated as small tight packets travelling inside the wall in the thickness direction. GWU wavelengths are on the order of the wall thickness or greater, and the wave packets occupy the whole wall thickness and travel in the areal direction along the wall. Thus, the GWU can propagate great distances along the wall area only slightly diminished, like light in optical fibers. Bulk waves propagate without dispersion, while GWU waves are dispersive. In GWU, different frequencies in the wave packet propagate at different velocities and pulses will change shape as they travel along. Finally, instead of the two wave modes as in standard UT, there are many modes in GWU.

The physics of guided waves was described by Lamb in 1917, and Mindlin in the 1950s & 1960s, but little technology in industrial container testing resulted until the early 1990s. As advanced microprocessors made the difficult GWU computations possible, there was an increased interest in the industrial application of GWU.

Currently, there are at least two GWU applications in container testing. The first is the container thickness measurement where the received pulse travels directly from the transmitter to the receiver along the container wall a known distance at a known velocity. Since the spacing between the transmitter and receiver is much greater than the transducer size, the GWU thickness measurement is much faster than the ultrasonic thickness gauge measurement. Note that the GWU wall thickness is an integrated wall thickness over the line between the transmitter and receiver. The other GWU application is for crack detection, e.g., where a single transducer is used as both the transmitter and receiver to listen to the GWU echoes from cracks in the wall. In both cases, the GWU measurements rely on the GWU waves whose energy is distributed through the whole wall thickness.

Since the GWU wave energy is distributed through the entire wall thickness, the GWU method is sensitive to both the container inner and outer wall surface conditions. The sensitivity of the GWU measurement to the outer wall surface can be adjusted by varying the wave mode and frequency selected. Paint and dust have little effect on the measurement due to the large impedance and stiffness mismatch to the container material.

However, the sensitivity of conventional UT and GWU is limited. MIC nodules, slimy fluid and foreign objects in the container can go undetected since they may not affect the waves.

In the present invention, a "leaky guided wave ultrasound" (LGWU) system is utilized. In the system, a transmitting transducer excites a guided wave, and part of its energy leaks into fluid in a pipe or other container. The leaking wave travels through the fluid, reflects off the container inner wall and enters the receiving transducer. The LGWU method measures both the direct field, and the leakage field inside the fluid generated by the guided ultrasonic waves. Since the leakage field interacts directly with the fluid and inner container wall, the LGWU method is able to reliably detect corrosion, MIC and other features on the container inner wall, as well as fluid composition, including foreign objects inside the fluid.

DESCRIPTION OF PREFERRED EMBODIMENTS

It will be understood that the methods and apparatus herein are used for examining, e.g., the inner walls and contents of any type of container (e.g., any fluid filled container). As used herein, the term "container" is intended broadly to apply to any structure that can be said to encompass a given volume, or even to define a portion of a given volume. Such structures include, without limitation, pipes and other conduits, whether partly or fully open or partly or fully closed, tanks, cylinders, plates, pressure vessels, etc. In general, when specifically referring to any of these (e.g., pipes) herein, it will be appreciated that similar methods, apparatus, devices systems, etc., can be applied to any similar structural form.

FIG. 1 shows a basic schematic of a leaky guided wave ultrasound (LGWU) system of the invention. One of skill will recognize a variety of features that may be substituted to achieve essentially similar results; however, for clarity, the following discussion focuses on this basic system.

The system, which interfaces, e.g., with fluid filled pipe or other container 1, comprises transmitting transducer coupling system 3, receiving transducer coupling system 4, RF amplifier 6, RF receiver gain 7 and filter 8 circuitry, computer 10 with plug-in arbitrary function generator 5, 2-channel A/D converter 9, and an energy field detection/display module 11. The output of arbitrary function generator 5 is connected to the input of RF amplifier 6. This output is optionally input into channel 1 of A/D converter 9 to provide a reference signal. The RF amplifier 6 output is connected to transmitting transducer 3. The receiving transducer is connected to the input of the RF receiver gain 7 and filter 8 circuitry. The output of the RF receiver is connected to the channel 2 input of A/D converter 9. Energy field detection/display module 11 controls the signal generation, acquisition and display functions. The energy field detection module optionally comprises an analog to digital converter, which converter converts direct or leakage field energy into digital format data. Arbitrary function generator 5 can, e.g., generate a pulse at a user defined frequency. Energy field detection/display module 11 can be e.g., a software module in computer 10, or module 11 can be a separate device with software elements.

Software and/or hardware present in energy field detection/display module 11 (this module can include software, firmware, hardware, or a combination thereof, for data analysis and/or display, including analog and/or digital display formats) controls function generator 5 to generate a tone burst pulse with selectable frequency, amplitude, shape, cycles in the pulse and pulsing rate. As noted, the module can include stand alone software or hardware (e.g., dedicated microprocessor hardware), or, commonly, can simply include software present in computer 10. The shaped tone burst pulse out of function generator 5 is sent to the channel 1 input of A/D converter 9 and displayed on the computer screen (depicted as the upper trace). The same pulse is also sent e.g., simultaneously, to the input of RF amplifier 6. After amplification, the pulse is then sent to wideband transmitting transducer 3 to excite the guided wave in the container wall. Part of the excited guided wave leaks into the fluid in the form of a bulk wave (leakage field), while the other part continues its propagation along the circumference in the metal wall (direct field). The leakage wave travels inside the fluid, reflects off the inner wall and enters back to the wideband receiving transducer 4 trailing the direct wave. The received signal is then amplified and filtered by gain 7 and filter 8 circuitry of the RF receiver.

The conditioned signal is then sent to channel 2 input of A/D converter 9, and displayed on the computer screen (depicted as the lower trace). Note that display/software for energy field detection/display module 11 can also define data acquisition parameters such as the A/D rate, total digitized time window, etc. Alternately, these parameters can be controlled separately, e.g., using a different module in computer 10, or a second computer.

A user can create a calibration wave, using the software, for each container wall thickness, diameter, and material. This wave can be displayed, allowing the user to visually compare the calibration wave with the wave from the container being inspected. This is a helpful component of the system, providing accuracy and reliability when in use by trained personnel. It should be noted that this form of display is novel to the present system.

For pipes or other containers of different OD and wall thicknesses, a specific group of frequencies and transducer coupling systems is selected to maximize the excitation of the leakage field from the well-known leakage theory of guided waves. The frequency range for LGWU wave generation is between about 100 kHz to about 1.5 MHz, with sensor angles between about 45° and about 70° from the normal to the container surface. The amount of the leakage energy is determined, e.g., by the frequency of the ultrasound, properties of the coupling medium and the wall material and thickness. If corrosion exists on the wall inner surface, both the direct and leakage fields are reduced. If there is an obstruction in the container, the leakage energy is reduced due to blockage and scattering. This phenomenon can be used to detect inner wall container features such as corrosion and MIC nodules on the inner wall, or ice due to frozen condensation water (ice which is free in solution can be detected as well, as a foreign object in the fluid), as well as the presence of denser fluids such as slimy fluid (or less dense fluids, such as hydrocarbon-based fluids), the existence of foreign objects in the fluid (ice, dirt, debris, organic matter, rodents, etc.), as well as fluid level in the container. Data analysis/display software for energy field detection/display module 11 analyzes the direct field energy, the leakage field energy and the ratio of leakage/direct field energy, and then classifies the condition of the container (of course, separate software modules can be substituted in place of a single software module).

Generally, the software controls the transmission and reception of the ultrasonic pulse, performs specific analyses to evaluate and categorize the container condition, and displays both raw signals and analysis results in a user friendly format. To measure properly, the type of container is input into a database which can be added to as necessary or desired. This database includes, e.g., the material, schedule and diameter of the container, etc.

A feature of the software optionally provides calibration. For example, by selecting a "CAL" button on the screen, a standard waveform for a new container of that material, schedule and diameter is displayed just above that of the container being tested. This provides the operator with a useful visual comparison to supplement the analysis algorithms. This becomes particularly helpful when the container schedule changes unexpectedly, as it often does, e.g., in older systems that have undergone repairs.

The following provides a basic flowchart/outline of the operations performed by an exemplar software module:

1. Select pipe or other container parameters (schedule and diameter).

2. Select measurement, e.g., thickness or obstruction.

3. Select calibration waveform (this is optional)

4. Acquire data: pulse shape and frequency are downloaded from an internal database; the pulse is sent out of the pulser board in the computer. The pulse is amplified and excites the transmitting transducer. The pulse is detected by the receiving transducer, fed to receiver electronics, and then fed into an analog to digital converter and stored in digital electronic format in the computer.

5. Analyze data: received waveform(s) is/are compared with calibration signal(s) and direct waves are compared to energies of multiple leaky waves as well as the direct wave.

6. Raw data is displayed as received signal(s) and analysis result(s).

7. Stored calibration pulse waveform for good container(s) are displayed.

In general, the LGWU method can be used on pipes or other containers without much surface preparation. For each measurement, the direct and leakage fields cover a significant portion of the container circumference. Therefore, only two or three measurements in the circumferential direction are needed to completely inspect the container inner wall and the fluid inside. Thus, the method can be used to determine the amount of any flow restriction as well as the existence of any occlusion in the container.

To detect fluid level, one moves the transducers axially above or below the fluid level. If the transducers are below the fluid level, the system records the existence of the leakage field. If above the fluid level, the leakage field is absent. For each axial position, a single measurement is sufficient to detect the existence of fluid inside the container (although, of course, multiple measurements can also be made, if desired).

Water-coupled wideband transducers, dry-coupled wideband transducers, and an air-coupled wideband transducer are all examples of appropriate transducers for the present invention. FIG. 2 shows three different ways of implementing LGWU transducer coupling system 3 and 4 in FIG. 1, and many others will be apparent to one of skill, in light of complete review of this disclosure. For the water-coupled system shown in FIG. 2, panel A, contact transducer 15 is mounted on wedge shoe 12 with ultrasonic gel in between. A bottom surface of shoe 12 is machined to match the contour of the container outer surface. In addition, water holes are drilled into the bottom surface. Water tubes are used to connect the water holes to water pump 13 in water bucket/container 16, and to vacuum pump 14 attached to the side of water bucket/container 16 above water line. Water pump 13 pumps water to the shoe bottom to provide coupling between the wedge shoe and container outer surface. Excess water is sucked up by vacuum pump 14 and flows back into water bucket 16. For the dry-coupled system shown in FIG. 2, panel B, immersion transducer 18 is placed inside a fluid-filled rubber wheel 17 (it will be appreciated that materials such as polymers, plastics or the like can be substituted for the rubber on the rubber wheel). The wheel rotates while the transducer sits at a fixed angle towards the container. The fluid couples the ultrasound from the sensor to the rubber wheel. The rubber on the outside surface of the wheel deforms to the outside diameter of the container, and is coupled to the container using a small amount of ultrasonic couplant.

An air-coupled system like that in FIG. 2, panel C can also be used. Air-coupled transducer 19, such as an electromagnetic transducer (EMAT), is placed at an appropriate distance above (or otherwise proximal to) the container.

The coupling system couples ultrasound out of the transmitting sensor and into the container to become guided waves propagating away from the system along the container wall. At the same time, it also couples the ultrasound traveling towards the receiving coupling system into the receiving transducer.

Accordingly, the leaky guided wave ultrasound (LGWU) system provides a fast and reliable device to detect inner wall container features such as corrosion, ice and MIC on the container inner wall, fluidic features such as fluid density and composition, ice, dirt and other foreign objects inside the fluid, and fluid level. These detection abilities are extremely useful in many industrial, commercial and even residential settings, i.e., essentially anywhere fluid filled containers are found. For example, without limitation, fire suppression systems, gas cylinders, water supply and removal (sewage) systems, refineries, water treatment facilities, petroleum supply stations and many others extensively utilize fluid filled containers.

As noted, while the above description contains many specific examples, these should not be construed as limitations on the scope of the invention, but rather as an exemplification of embodiments thereof. Many other variations are possible and will be apparent to one of skill upon review of this disclosure. For example, one can perform the fluid level detection using a more efficient configuration by placing the transducers axially rather than circumferentially. If the transducers are below the fluid level, the direct wave energy is the smallest due to maximum leakage. On the other hand, if the transducers are above the fluid level, the direct wave energy is the strongest due to the absence of leakage. Another example is to apply the same LGWU system to inspect fluid containers of non-circular shapes, such as cubes and cones (i.e., conic and cubic shapes, or any other regular or irregular shapes).

Other uses of the LGWU method include detection of objects or materials inside or behind other structures near or attached to a wall. For example, the trays inside a distillation column, vanes and partitions inside a tank, hat stiffeners in an aircraft wing filled with fuel, reinforcements and other attachments for walls of a fluid container, etc. The advantage of using the LGWU method in those applications is that one can determine whether something is attached to the wall anywhere on the circumference, without having to inspect the entire circumference point by point. This approach is much faster, more reliable and more versatile than standard UT point-by-point methods.

Variations of transducer coupling systems 3 and 4, other than those specifically described above, can also be used. These include, but are not limited to, dry couplant, laser, electrostatic transducers, air scanners, rollers, touch and release fixtures, back reflected energy with a single transducer etc. Similarly, plug-in function generator 5 can comprise or be replaced by a stand-alone analog function generator, and computer 10 with plug-in A/D converter 9 can also be substituted, e.g., by a digital or analog oscilloscope. The system optionally includes an analog energy detector and analog or digital display.

The foregoing description of embodiments of the invention has been presented for purposes of illustration and description. The description is not intended to be exhaustive or to limit the invention to the precise form disclosed, and many modifications and variations are possible in light of the above teaching. Such modifications and variations which may be apparent to a person skilled in the art are within the scope of this invention. All patent documents and publications cited above are incorporated by reference in their entirety for all purposes to the same extent as if each item were so individually denoted.

What is claimed is:

1. A method for detecting container features, or fluids or other materials inside a fluid filled container, by leaky guided wave ultrasound (LGWU), the method comprising:
   (a.) placing a transmitting transducer and a receiving transducer at longitudinal or circumferential positions of a fluid-filled container;
   (b.) generating guided waves using a shaped tone burst pulse at a specified frequency; and,
   (c.) measuring both a direct field and a leakage field, thereby providing an indication of existence of features, fluid or materials inside of the fluid filled container.

2. The method of claim 1, wherein the container comprises one or more of: a pipe, a conduit, a tank, a barrel, a drum, a cylinder, and a plate.

3. The method of claim 1, wherein the container comprises one or more of: a circular region, a conic region, and a cubic region.

4. The method of claim 1, wherein the container features, fluids or other materials comprise one or more of: corrosion on the inner wall of the fluid-filled container, MIC on the inner wall of the fluid-filled container, ice on the inner wall of the fluid filled container, ice in the fluid in the fluid filled container, foreign material in the fluid in the fluid filled container, fluid level of the fluid in the fluid filled container, or fluid density of the fluid in the fluid filled container.

5. The method of claim 4, wherein said corrosion comprises pitting or loss of wall material on the container inner wall.

6. The method of claim 4, wherein said MIC comprises microbiologically-induced corrosion.

7. The method of claim 1 wherein said fluid or other material comprises one or more of: a floating solid, a slimy fluid, or a material attached to the inner wall.

8. The method of claim 1, wherein said transducer comprises a water-coupled wideband transducer, a dry-coupled wideband transducer, or an air-coupled wideband transducer.

9. The method of claim 1, wherein said guided waves are waves excited at a selected frequency and angle to maximize the leakage field for selected container ODs and materials.

10. The method of claim 1, wherein said measuring includes recording and analyzing the direct field energy, the leakage field energy and the energy ratio of leakage field energy to direct field energy.

11. The method of claim 1, wherein the amplitude of a given phase point on the tone burst is selected or modulated.

12. The method of claim 1, wherein said direct field is part of the received signal due to guided wave propagation along the container.

13. The method of claim 1 wherein said leakage field is part of the received signal for a leaky bulk wave propagating inside the fluid.

14. An integrated system for detecting container features, or fluids or other materials inside a fluid filled container, by leaky guided wave ultrasound (LGWU), the system comprising:
   (a.) a transmitting transducer and a receiving transducer placed at longitudinal or circumferential positions of a fluid-filled container;
   (b.) a guided wave generator which produces a shaped tone burst pulse at a specified frequency; and,
   (c.) an energy field detection module for measuring both a direct field and a leakage field, which measurement provides an indication of container features or materials inside the fluid filled container.

15. The integrated system of claim 14, wherein the container comprises one or more of: a pipe, a tank, a barrel, a drum, a cylinder, and a plate.

16. The integrated system of claim 14, wherein the container comprises one or more of: a circular region, a conic region, and a cubic region.

17. The integrated system of claim 14, wherein the container features, fluids or other materials comprise one or more of: corrosion on the inner wall of the fluid-filled container, MIC on the inner wall of the fluid-filled container, ice on the inner wall of the fluid filled container, ice in the fluid in the fluid filled container, foreign material in the fluid in the fluid filled container, fluid level of the fluid in the fluid filled container, or fluid density of the fluid in the fluid filled container.

18. The integrated system of claim 14, comprising a computer or computer readable medium comprising an instruction set for controlling the transmitting transducer, or the guided wave generator.

19. The integrated system of claim 14, the energy field detection module comprising a computer or computer readable medium comprising an instruction set for measuring the direct field and the leakage field.

20. The integrated system of claim 14, the energy field detection module comprising a computer or computer readable medium comprising an instruction set for measuring the direct field and the leakage field and an additional instruction set for reporting the results of the measurement to a user.

21. The integrated system of claim 20, said instruction set comprising instructions for recording and analyzing the direct field energy, the leakage field energy and the energy ratio of leakage field energy to direct field energy.

22. The integrated system of claim 14, wherein said transducer comprises a water-coupled wideband transducer, a dry-coupled wideband transducer, or an air-coupled wideband transducer.

23. The integrated system of claim 14, wherein the energy field detection module comprises an analog to digital converter, which converter converts direct or leakage field energy into digital format data.

24. The integrated system of claim 23, the detection module comprising a digital display, which digital display provides a user-viewable display of information in the digital format data.

25. The integrated system of claim 14, wherein the energy field detection module comprises an analog energy detector and an analog display.

26. The integrated system of claim 14, the detection module comprising means for measuring the direct and leakage field.

27. A device for detecting container features, or fluids or other materials inside a fluid filled container, by leaky guided wave ultrasound (LGWU), the device comprising:
    (a.) a transmitting transducer and a receiving-transducer configured to be placed at circumferential or longitudinal positions of a fluid-filled container;
    (b.) a guided wave generator which produces a shaped tone burst pulse at a specified frequency; and,
    (c.) means for measuring both a direct field and a leakage field, thereby providing an indication of existence of corrosion and MIC on the container inner wall, foreign objects inside the fluid and fluid level.

28. The device of claim 27, wherein the container comprises one or more of: a pipe, a tank, a barrel, a drum, a cylinder, and a plate.

29. The device of claim 27, wherein the container comprises one or more of: a circular region, a conic region, and a cubic region.

30. The device of claim 27, wherein the container features, fluids or other materials comprise one or more of: corrosion on the inner wall of the fluid-filled container, MIC on the inner wall of the fluid-filled container, ice on the inner wall of the fluid filled container, ice in the fluid in the fluid filled container, foreign material in the fluid in the fluid filled container, fluid level of the fluid in the fluid filled container, or fluid density of the fluid in the fluid filled container.

31. The device of claim 27, further comprising a computer or computer readable medium comprising an instruction set for measuring the direct field and the leakage field and an additional instruction set for reporting the results of the measurement to a user.

32. The device of claim 31, said instruction set comprising instructions for recording and analyzing the direct field energy, the leakage field energy and the energy ratio of leakage field energy to direct field energy, or a ratio of another suitable wave characteristic of the leakage field to the direct field.

33. The device of claim 32, wherein the other suitable wave characteristic is amplitude of a given phase point on the tone burst.

34. The device of claim 27, wherein said transducer comprises a water-coupled wideband transducer, a dry-coupled wideband transducer, or an air-coupled wideband transducer.

35. The device of claim 27, further comprising a computer with a plug-in arbitrary function generator and analysis/display software.

36. The device of claim 35 further comprising a 2-channel A/D converter.

37. The device of claim 35, wherein the arbitrary function generator generates a pulse at a user-defined frequency.

38. The device of claim 35, wherein the arbitrary function generator generates a pulse at a user-defined frequency and wherein an output of the arbitrary function generator is connected to a first channel input of the A/D converter.

39. The device of claim 22, further comprising a transmitting transducer coupling system, a receiving transducer coupling system, a RF amplifier, a RF receiver gain and filter circuitry, a computer with a plug-in arbitrary function generator, a 2-channel A/D converter, and an analysis/display software.

40. The device of claim 39, wherein the arbitrary function generator generates a pulse of user-defined frequency and wherein:
    the output of the arbitrary function generator is connected to a first channel input of the A/D converter and to an input of the RF amplifier;
    the RF amplifier output is connected to the transmitting transducer;
    the receiving transducer is connected to an input of the RF receiver gain and filter circuitry;
    the output of the RF receiver is connected to a second channel input of the A/D converter; and,
    the data analysis/display software controls signal generation, acquisition and display functions.

* * * * *

UNITED STATES PATENT AND TRADEMARK OFFICE
CERTIFICATE OF CORRECTION

PATENT NO. : 6,367,328 B1  Page 1 of 1
DATED : April 9, 2002
INVENTOR(S) : Michael R. Gorman et al.

It is certified that error appears in the above-identified patent and that said Letters Patent is hereby corrected as shown below:

<u>Title page,</u>
Item [60], Related U.S. Application Data, should read as follows:
-- Provisional application No. 60/209,796, filed June 5, 2000. --

Signed and Sealed this

Eighth Day of October, 2002

Attest:

Attesting Officer

JAMES E. ROGAN
*Director of the United States Patent and Trademark Office*

UNITED STATES PATENT AND TRADEMARK OFFICE
CERTIFICATE OF CORRECTION

PATENT NO. : 6,367,328 B1
DATED : April 9, 2002
INVENTOR(S) : Michael R. Gorman et al.

It is certified that error appears in the above-identified patent and that said Letters Patent is hereby corrected as shown below:

The title page should be deleted and substitute thereof the attached title page.

<u>Drawings,</u>
Delete drawing sheets 1 & 2, and substitute therefore the drawing sheets, consisting of Figs. 1 & 2, as shown on the attached pages.

Signed and Sealed this

Eighteenth Day of November, 2003

JAMES E. ROGAN
*Director of the United States Patent and Trademark Office*

United States Patent
Gorman et al.

(10) Patent No.: US 6,367,328 B1
(45) Date of Patent: Apr. 9, 2002

(54) NONINVASIVE DETECTION OF CORROSION, MIC, AND FOREIGN OBJECTS IN FLUID-FILLED CONTAINERS USING LEAKY GUIDED ULTRASONIC WAVES

(75) Inventors: Michael R. Gorman, Englewood; Steven M. Ziola, Littleton; Wei Huang, Highlands Ranch, all of CO (US)

(73) Assignee: Digital Wave Corporation, Englewood, CO (US)

( * ) Notice: Subject to any disclaimer, the term of this patent is extended or adjusted under 35 U.S.C. 154(b) by 0 days.

(21) Appl. No.: 09/613,704

(22) Filed: Jul. 11, 2000

Related U.S. Application Data (60) Provisional application No. 60/143,366, filed on Jul. 12, 1999, provisional application No. 60/203,661, filed on May 12, 2000, and provisional application No. 60/209,796, filed on Jun. 7, 2000.

(51) Int. Cl.$^7$ .................................................. G01N 29/00
(52) U.S. Cl. ..................... 73/592; 73/598; 73/290 R; 73/622; 73/624; 73/597; 73/644
(58) Field of Search .......................... 73/570, 597, 599, 73/52, 587, 590, 290 R, 620, 622, 624, 643, 644, 600, 598, 592

(56) References Cited

U.S. PATENT DOCUMENTS

| | | | | |
|---|---|---|---|---|
| 4,843,884 A | * | 7/1989 | House et al. | 73/622 |
| 4,890,496 A | * | 1/1990 | Birring et al. | 73/597 |
| 5,031,456 A | * | 7/1991 | Askwith et al. | 73/587 |
| 5,295,120 A | * | 3/1994 | McShane | 367/188 |
| 5,526,689 A | * | 6/1996 | Coulter et al. | 73/592 |
| 5,723,791 A | * | 3/1998 | Koch et al. | 73/597 |
| 5,734,588 A | * | 3/1998 | Rose et al. | 73/644 |
| 5,767,410 A | * | 6/1998 | Lareau et al. | 73/623 |
| 5,922,945 A | * | 7/1999 | Allmaras et al. | 73/52 |
| 5,970,434 A | * | 10/1999 | Brophy et al. | 73/584 |
| 6,105,431 A | * | 8/2000 | Duffil et al. | 73/624 |
| 6,186,004 B1 | * | 2/2001 | Kaduchak et al. | 73/596 |

\* cited by examiner

*Primary Examiner*—Hezron Williams
*Assistant Examiner*—Jacques Saint-Surin
(74) *Attorney, Agent, or Firm*—Jonathan Alan Quine; Quine Intellectual Property Law Group, P.C.

(57) ABSTRACT

Ultrasonic energy in the form of guided waves is launched into the wall of a fluid-filled container. The guided wave propagates around the circumference of the container from a transmitting transducer to a receiving transducer. Part of the guide wave energy leaks into the fluid in the form of bulk waves, reflects off the inner wall on the other side and enters back to the receiving transducer trailing the direct wave. Analysis of the received waves determines the presence of corrosion pitting and MIC nodules on the container inner wall, and fluid level. In addition, it determines whether foreign objects are inside the container. The guided waves are created with wideband transducers excited at certain frequencies that depend on the material and geometry of the part being measured. The leakage energy is maximized with a shaped tone burst pulse at the specified frequency. The energy and energy ratio of both the direct and leakage fields are measured and related to the container inner wall condition and the presence of any foreign objects in the fluid.

40 Claims, 2 Drawing Sheets

Fig. 1

Fig. 2